United States Patent [19]

Schwengers et al.

[11] Patent Number: 4,693,974
[45] Date of Patent: Sep. 15, 1987

[54] PROCESSES FOR PRODUCING LEUCROSE

[75] Inventors: Dieter Schwengers, Dormagen; Herta Benecke, Frechen-Grefrath, both of Fed. Rep. of Germany

[73] Assignee: Pfeifer & Langen, Cologne, Fed. Rep. of Germany

[21] Appl. No.: 913,268

[22] Filed: Sep. 29, 1986

Related U.S. Application Data

[62] Division of Ser. No. 809,714, Dec. 17, 1985.

[30] Foreign Application Priority Data

Dec. 19, 1984 [DE] Fed. Rep. of Germany ....... 3446380

[51] Int. Cl.$^4$ ...................... C12P 19/18; A23G 3/00; A23L 1/236
[52] U.S. Cl. .................................... 435/97; 426/548; 426/658
[58] Field of Search .......................................... 435/97

[56] References Cited

PUBLICATIONS

Parnaik et al., Febs Letters, vol. 150, No. 2, pp. 482–484 (Dec. 1982).

Primary Examiner—Lionel M. Shapiro
Attorney, Agent, or Firm—Wegner & Bretschneider

[57] ABSTRACT

Sweetening agents for human and animal foods in the solid or liquid states contain at least 50% by weight of leucrose. They may additionally contain one or more sweetening agents selected from the group consisting of artificial sweeteners and sugar surrogates. The leucrose is produced by reaction of saccharose with $\alpha$-(1-6)-glucosyl transferase in the presence of at least 100 mmoles of fructose per 1,000 I.U. of enzyme, and at least a partial separation of the dextrans and iso-malto-oligosaccharides. Leucrose may be prepared by this method having a purity of at least 98% and may be used as a non-cariogenic, metabolically fully utilizable sweetening agent with good compatibility which is also suitable for diabetics.

2 Claims, No Drawings

PROCESSES FOR PRODUCING LEUCROSE

This application is a division of Ser. No. 809,714, filed Dec. 17, 1985.

The present invention relates to a sweetening agent for foods, luxury foods and animal foods in the solid or liquid states. The invention further provides processes for producing said sweetening agent. Further provided is the use of the sweetening agent, such as in a purified form, as a non-cariogenic, metabolically fully utilizable, highly compatible sweetening agent which is also suitable for diabetics.

Prior to the present invention, leucrose (5-O-α-D-glucopyranosyl-D-fructose) was known in the art only as an undesirable by-product in the synthesis of dextrans by the action of *Leuconostoc mesenteroides* on saccharose solutions; cf. U. Behrens, M. Ringpfeil, Mikrobielle Polysaccharide, AkademieVerlag Berlin 1964, pp. 37-39. From the investigations conducted by Robyt and Eklund, Carbohydrate Research 121 (1983), pp. 279-286, it is apparent that fructose, at a molar ratio of fructose:saccharose of 1:1 yields about 85% dextrans and 2.2% of a mixture comprising leucrose and isomaltulose.

A recovery and purification of the leucrose from these mixtures is extremely difficult, so that the properties of this disaccharide prior to the present invention have not been studied. As a result, those publications mentioning this sugar have provided only very limited information concerning its properties. The separation and purification of leucrose is particularly difficult. This is because in the conventional polystyrene sulfonate cation exchangers of proven value for technical scale operations, the leucrose in its calcium form behaves chromatographically like glucose and saccharose. Thus, in practice, leucrose previously could not be separated from these two components.

PRIOR ART

In J. Amer. Chem. Soc. 78 (1956), pp. 2514-2518, leucrose is described as a by-product of dextran production. It was generated at a rate of 7.9%, based on the saccharose starting material; cf. p. 2516, column 2, 4th full paragraph. In the section of this article entitled "Properties of Leucrose" it is taught that leucrose is not very sweet. This statement is of limited value to one skilled in the art, as it does not provide a recitation of the relative sweetening power of leucrose in comparison to another sugar such as saccharose. The term a "not very sweet" sugar could be understood to apply to lactose, which has about 30% of the sweetening power of saccharose. Glucose having a sweetening power of about 50% of that of saccharose is still perceived as being sweet. Lactose, due to its low sweetening power, in general is not used as a sweetener, but mostly as a filler, aroma-enhancing agent, and tablet filler.

In quantitative testing recently conducted by Applicants to determine the relative sweetening power of various sugars, it was discovered unexpectedly that the sweetening power of the leucrose actually is about 50 to 60% of that of saccharose and, thus, even above the sweetening power of glucose. The belief expressed in the art prior to this invention was that leucrose was "not very sweet". As a result, no one in the foods industry has had the motivation to develop a production process for leucrose, as it was perceived to be a mere by-product of no practical use as a sweetner.

In Biochem. J. 79 (1961), pp. 549, 553, there has been described the formation of by-products in the course of the dextran formation by *Streptococcus bovis*. Leucrose was obtained in a yield of 1.5% based on saccharose; cf. Table 1. No statements were made as to the properties or possible uses of the leucrose.

In Carbohydrate Research 62 (1978), pp. 281-287, there has been described chemical synthesis of leucrose starting from glucose. The total yield of this synthesis process is about 3%. While a "yield" of 53% is recited, it should be noted that this applies only to the last step of 13 steps. Because of the low yield, this process of synthesis amounts to a mere scientific curiosity. Yields at such low levels cannot be considered as an economic procedure for the synthesis of leucrose.

In "Die Nahrung", Vol. 8 (1964), pp. 523-531, saccharides of dextran effluents and the conversion thereof in the animal intestinal tract were studied. Particular attention was given to leucrose. These dextran effluents approximately correspond to those mentioned in J. Amer. Chem. Soc. 78 (1956), pp. 2514-2518. Therefore, it may be assumed that a yield of about 8%, based on saccharose, was obtained. In the introduction to this reference there is found an indication that the mother liquors produced in the dextran production may be used for dietetic purposes, referring, no doubt, to its major component, fructose. This sugar is well known as being appropriate for use in human nutrition. It was the object of this investigation to determine whether the further components as contained in the dextran effluents would be physiologically compatible in an effort to avoid the requirement for separation.

INVENTION

For the first time, a technically feasible process for the production of useful amounts of pure leucrose has been devised. Furthermore, in the course of the investigation by the inventors of the properties of leucrose, it has been established that this substance can be used as a non-cariogenic, metabolically fully utilizable, physiologically compatible sweetening agent. Further, this sugar is especially suitable for use in diabetic individuals.

It has been discovered that, with leucrose, no acid formation is observed in the standard caries test using *Streptococcus mutans*. Furthermore, as leucrose is not an acceptor for glucose, no dextrans will be formed during the mastication process. This avoids the formation of tooth plaque. Experiments using intestinal bacteria have shown that leucrose is cleaved at a rate which is about 1/5 to ⅓ of the rate of maltose. Thus, leucrose is a fully metabolically utilizable carbohydrate, which, however, has a smaller rate of cleavage as compared to saccharose and maltose. Thus, it does not produce the typical steep increase in the blood glucose level caused by saccharose or maltose. It may be expected that leucrose, in contrast to saccharose and maltose, will not stimulate insulin secretion to the levels of saccharose and maltose, if it does so at all. Moreover, due to cleavage caused by intestinal bacteria, glucose directly influencing the blood glucose level is only formed as 50% of the leucrose, the other 50% being fructose. The fructose is known, at least within certain limits, not to burden the blood glucose level. Fructose is mostly metabolized via the liver and will participate in the glucose synthesis. Leucrose is, therefore, particularly suitable for use in the diets of diabetics.

The leucrose degradation by intestinal bacteria nevertheless takes place so rapidly that larger amounts thereof do not enter the large intestine where they may cause diarrhoea due to retarded metabolism. This advantage is of particular significance for children and diabetics. It has been confirmed by the more exact measured results as now available that leucrose is cleaved only at a rate of about 38% the rate of saccharose and, thus, is excellently suitable as a sugar surrogate for diabetics.

As a consequence of the newly developed method, leucrose can be economically produced and purified on a large scale. It has become possible to use this disaccharide as a sweetening agent for foods, luxury foods and animal foods in the solid or liquid states. In these uses, the content of leucrose in the sweetening agent should be at least 50% by weight. According to the processes of the invention, it is a simple matter to produce leucrose at a purity of at least 98%. In the use of leucrose as a non-cariogenic, metabolically fully utilizable, well compatible sweetening agent which is also suitable for diabetics, a purity of at least 95% by weight would suffice.

In the process according to the invention, leucrose is formed as a mixture with dextrane and iso-malto-oligosaccharides as well as some fructose. The dextrans and iso-malto-oligosaccharides at least in part are readily separable, so that leucrose is obtained at a content of at least 50% by weight. Since fructose, as well as lower iso-malto-oligosaccharides, are usable as a sweetening agent, the mixtures formed of leucrose, fructose and lower iso-malto-oligosaccharides may be directly used for a number of intended uses. However, it is possible to separate the fructose as well as the dextrans and iso-malto-oligosaccharides chromatographically from leucrose to such a degree that leucrose is obtained with purity of at least 95% by weight, and preferably of 98% by weight.

If desired, leucrose may also be mixed with other known sweeteners such as saccharin, cyclamate, acesulfam K, aspartame and talin. For certain other uses leucrose mixed with natural sugar substitutes such as sorbitol, mannitol, maltitol, xylitol, Palatinit ® and Lycasin ® may be employed.

The process according to the invention for the production of leucrose having a purity of at least 50% by weight is characterized in that saccharose is reacted with α-(1–6)-glycosyl transferase in the presence of at least 100 mmoles of fructose per 1,000 I.U. of enzyme, and the dextrans and iso-malto-oligosaccharides are at least partially removed. It is preferred that more than 300 mmoles of fructose to be employed per 1,000 I.U. of enzyme. The reaction is preferably carried out in a temperature range of from 265 K. to 310 K. and at a pH value of from 4.5 to 8.0. The saccharose concentration is chosen to be as high as possible for reasons of economics. Basically, concentrations as high as 60% of saccharose are applicable. However, at such high saccharose concentrations the rate of reaction is reduced. Concentrations of less than 20% result in lower yields and require an unnecessary input of energy for the subsequent workup procedure. Thus, it is preferred to operate at concentrations of from 35% to 50% of saccharose.

The fructose employed as acceptor is regenerated from saccharose in the course of the process. As a result, during the process the fructose concentration actually remains constant. Glucose is a substantially better acceptor, so that the glucose formed very rapidly undergoes further reaction to form iso-malto-oligosaccharides and dextrans. Thus, upon termination of the reaction, virtually no saccharose and no glucose remain. This eliminates the need for their separation. Dextrans and iso-malto-oligosaccharides may at least in part be separated from the mixture by any of several methods known in the art, for example by chromatography. By means of polystyrene sulfonate cation exchangers in the calcium salt form, it is even possible to virtually completely separate these by-products from the fructose fraction.

The process is preferably carried out by adding the aqueous saccharose solution to the mixture comprising fructose and enzyme in such a manner that the speed of the conversion of the added saccharose is optimized. This results in the saccharose being present at a low concentration in the final reaction mixture.

Another preferred embodiment employs glycosyl transferase either fixed to a carrier or included in a porous carrier. Bonding the enzyme to a carrier may be effected by any conventional method of bonding an enzyme to a carrier if the bonding activity of the enzyme is not decreased too severely. The enzyme may also be used in a porous carrier. For example, it may be incorporated as beads in alginate, and in this form it may be reacted with the fructose and saccharose. At least 100 mmoles, and preferably 300 mmoles, of fructose should be present per 1,000 I.U. of the enzyme. According to the invention, the yields of leucrose, based on saccharose, are 40% or more. The dextrans and iso-malto-oligosaccharides may be used in the conventional manner to increase the economic efficiency of the process.

Separating procedures, more specifically, chromatography using "size exclusion gels" or using polystyrene sulfonate cation exchanger resins in the calcium salt form, are applicable. More particularly, the dextrans and the higher molecular weight iso-malto-oligosaccharides can already be advantageously removed prior to the chromatography, e.g. by a membrane separation procedure such as ultrafiltration. More particularly, the chromatography using polystyrene sulfonate cation exchanger resins in the calcium salt form also allows fructose to be separated. If desired, fructose may be recycled into the process, as it is always reproduced in the same amount and, thus, apparently, acts like a catalyst.

The process according to the invention for producing and purifying the leucrose and the use thereof are further illustrated by the following examples. These examples are presented by way of illustration only, and in no way limit the breadth of the invention as taught herein.

EXAMPLE 1

4,000 g of crystalline fructose are dissolved at 298 K. in 6 l of an aqueous solution of the enzyme α-(1–6)-glucosyl transferase (dextran sucrase) having an activity of 7,500 I.U./l. The pH of the solution is 5.4. To this solution 30 l of a 40% saccharose solution having a pH of 5.4 are added. After 48 h, the saccharose content is less than 1% of the dry matter, and the leucrose content is 30.1%, corresponding to yield of 40.1%, based on the saccharose employed as the starting material.

EXAMPLE 2

40 ml of a dextran sucrase solution having an activity of 320 I.U. is stirred into a 4% sodium alginate solution.

The enzyme/alginate solution is added dropwise from a pipette into a 1% calcium chloride solution whereafter bead-like particles are formed by gellation of the alginate. These are washed out with distilled water. The alginate beads containing dextran sucrase are charged into a column to yield a gel bed of 196 ml. The enzyme activity is 1.3 I.U./ml of alginate gel.

Through said gel bed there are passed by pumping 8 ml/h of an aqueous saccharose/fructose solution containing 10 g of fructose and 45 g of saccharose per 100 g of solution. In the solution effluent from the gel bed there are contained 32.8% of leucrose, corresponding to yield of 40.0%, based on the saccharose.

EXAMPLE 3

18 kg of an aqueous leucrose solution obtained according to Example 1 and having a dry matter content of 35% is charged onto a separating column 6 m in height containing 190 l of polystyrene sulfonate cation exchanger and loaded with calcium. By supplying 35 l/h of distilled water, the saccharides charged onto the separating column are eluated. After fore-runnings comprising 51 l, the subsequent 38 l fraction contain some dextran and iso-malto-oligosaccharides in the eluation.

The 3 l fraction contains 112 g of leucrose besides 39 g of other saccharides; the subsequent 12 l fraction contains 1041 g of leucrose having a purity of about 96.1%. Within the next 3 l, another 153 g of leucrose in combination with 50 g of fructose and 2 g of glucose are eluated.

The thus obtained leucrose solutions may be directly used as sweeteners, if desired. They may also be further thickened to from a syrup. Solid leucrose, for example, is obtained by lyophilization of the solutions.

EXAMPLE 4

The leucose fraction as obtained in accordance with Example 3, which had been brought to a purity of 98.1% by means of a second chromatographic purification step, are tested for acid formation using Streptococcus mutans NCTC 10449. In the course thereof, the proton production is measured by registration of the pH drop in the acidification test as well as by alkali consumption (at constant pH) by automatic back titration. It is found that leucrose does not form acid. Since leucrose is a poor substrate for glucose, no dextrans are formed either. Tests using intestinal bacteria have resulted in the finding that the rate of leucrose degradation as compared to the degradation of maltose is about 1/5 to $\frac{1}{3}$. Thus, the degradation products fructose and glucose are already available in the small intestine and can be fully utilized metabolically. Virtually no undegraded leucrose will get into the large intestine.

EXAMPLE 5

2,000 g of cyrstalline fructose are dissolved at 298 K. in 1.6 l of an aqueous solution of the enzyme $\alpha(1-6)$-glucosyl transferase (dextran sucrase) having an activity of 7,500 I.U./l. The pH of the solution is 5.4. To this solution 13 l of an aqueous saccharose solution containing 5,200 g of saccharose are added by pumping during 70 hours. 2 hours after completion of the saccharose addition the saccharose content is less than 1% of the dry matter of the reaction mixture, and the leucrose content is 38.1%, corresponding to yield of 52.7%, based on the saccharose employed as the starting material.

The leucrose solution having been thickened to a dry substance content of 75 to 80%, is seeded with seed crystals and slowly cooled (at a rate of 1° to 3° C./h). Thus, leucrose is obtained as the monohydrate in the form of rhombic crystals; melting point 159°–160° C.; $[\alpha]_D^{20} = -6.8°$.

What is claimed is:

1. A process for producing leucrose having a purity of at least 50% by weight, characterized in that saccharose is reacted with $\alpha$-(1–6)-glucosyl transferase in the presence of at least 100 mmoles of fructose per 1,000 I.U. of enzyme, and the dextrans and iso-malto-oligosaccharides are at least partially separated.

2. The process according to claim 1, characterized in that, in order to increase the purity to at least 95% by weight, the leucrose is chromatographically separated from the fructose and the iso-malto-oligosaccharides.

* * * * *